US011839513B2

(12) United States Patent
Cuscuna

(10) Patent No.: US 11,839,513 B2
(45) Date of Patent: Dec. 12, 2023

(54) ULTRASOUND PROBE WITH CABLE RETENTION USING ELASTOMERIC INSERT

(71) Applicant: KONINKLIJKE PHILIPS N.V., Eindhoven (NL)

(72) Inventor: Dino Francesco Cuscuna, Reading, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 190 days.

(21) Appl. No.: 17/613,123

(22) PCT Filed: May 25, 2020

(86) PCT No.: PCT/EP2020/064357
§ 371 (c)(1),
(2) Date: Nov. 22, 2021

(87) PCT Pub. No.: WO2020/239654
PCT Pub. Date: Dec. 3, 2020

(65) Prior Publication Data
US 2022/0202392 A1    Jun. 30, 2022

Related U.S. Application Data

(60) Provisional application No. 62/852,460, filed on May 24, 2019.

(51) Int. Cl.
*A61B 8/00* (2006.01)
(52) U.S. Cl.
CPC .......... *A61B 8/4444* (2013.01); *A61B 8/4488* (2013.01); *A61B 8/4427* (2013.01)
(58) Field of Classification Search
CPC ......... A61B 8/4444; H01B 7/18; H01B 7/189
See application file for complete search history.

(56) References Cited

U.S. PATENT DOCUMENTS

| 4,988,838 A | 1/1991 | Kirtland |
| 5,882,310 A | 3/1999 | Marian, Jr. |

(Continued)

FOREIGN PATENT DOCUMENTS

| DE | 102016214583 A1 | 2/2018 |
| FR | 2730964 A1 | 8/1996 |
| JP | 2016093307 A | 5/2016 |

OTHER PUBLICATIONS

International Search Report and Written Opinion for PCT/EP2020/064357; dated Sep. 4, 2020.

*Primary Examiner* — Colin T. Sakamoto
*Assistant Examiner* — Tommy T Ly

(57) ABSTRACT

An ultrasound probe includes a housing configured for handheld operation by a user, a transducer array coupled to the housing and configured to obtain ultrasound data, and a cable coupled to the housing. The cable includes a conduit and a plurality of electrical conductors in communication with the transducer array. The ultrasound probe also includes an elastomeric insert disposed within the housing. The elastomeric insert includes a compressed state and an uncompressed state. The elastomeric insert is in contact with the plurality of electrical conductors such that application of a force on the cable causes the plurality of electrical conductors to compress the elastomeric insert into the compressed state and such that, upon cessation of the force on the cable, the elastomeric insert moves the plurality of electrical conductors while returning to the uncompressed state. Associated methods, devices, and systems are also provided.

15 Claims, 14 Drawing Sheets

(56) References Cited

U.S. PATENT DOCUMENTS

| | | | |
|---|---|---|---|
| 5,961,465 | A | 10/1999 | Kelly, Jr. et al. |
| 8,292,247 | B2 | 10/2012 | Fuller et al. |
| 2004/0114313 | A1 | 6/2004 | Mata et al. |
| 2013/0187012 | A1 | 7/2013 | Blakeley et al. |
| 2015/0209009 | A1 | 7/2015 | Huang et al. |
| 2016/0126445 | A1 | 5/2016 | Kiyose |

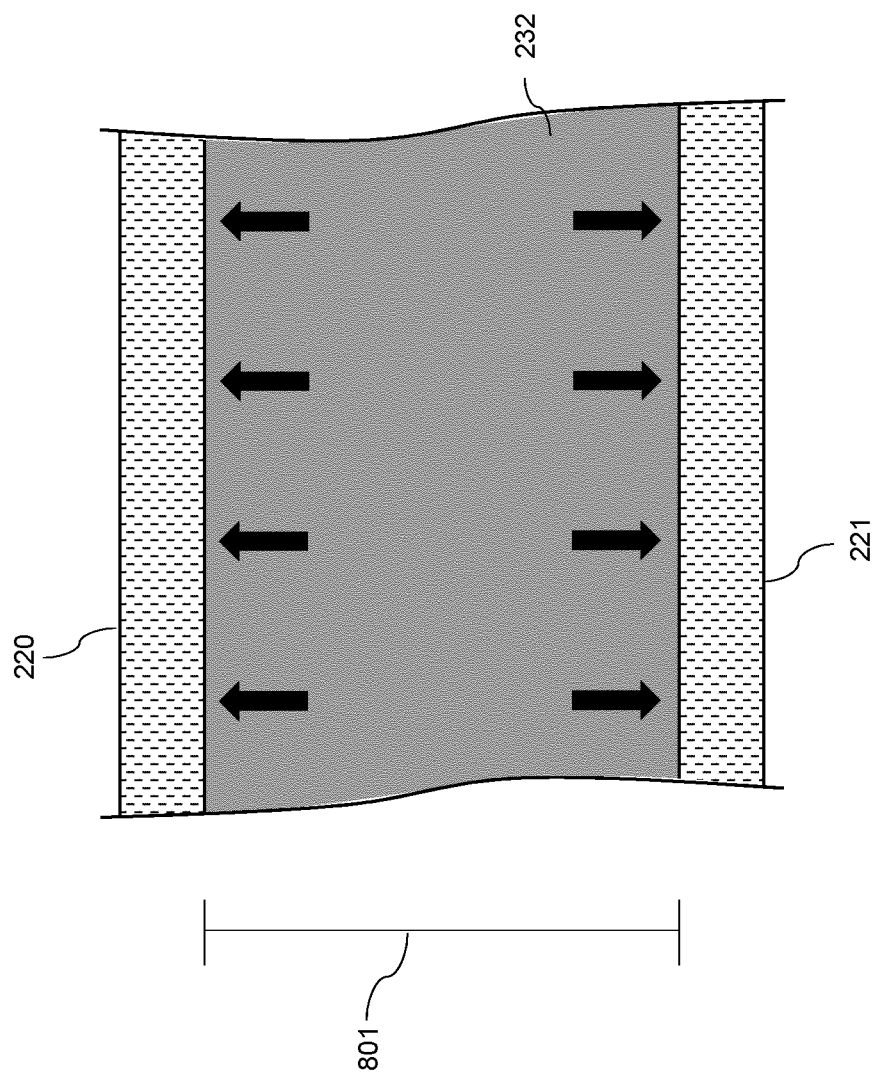

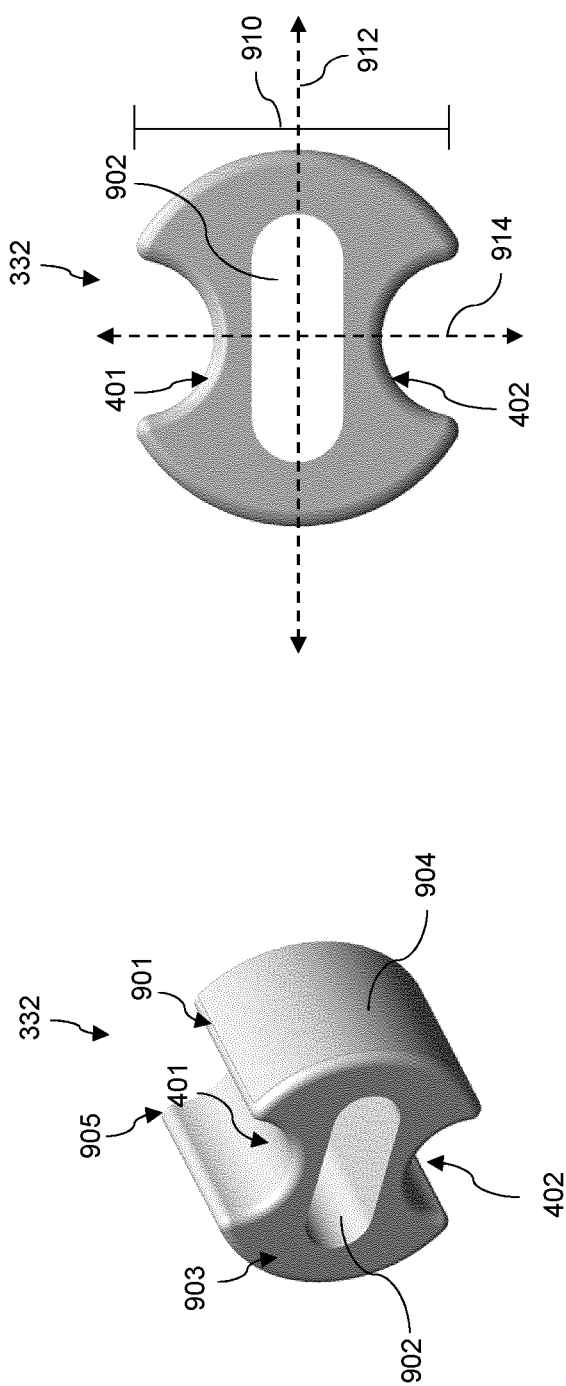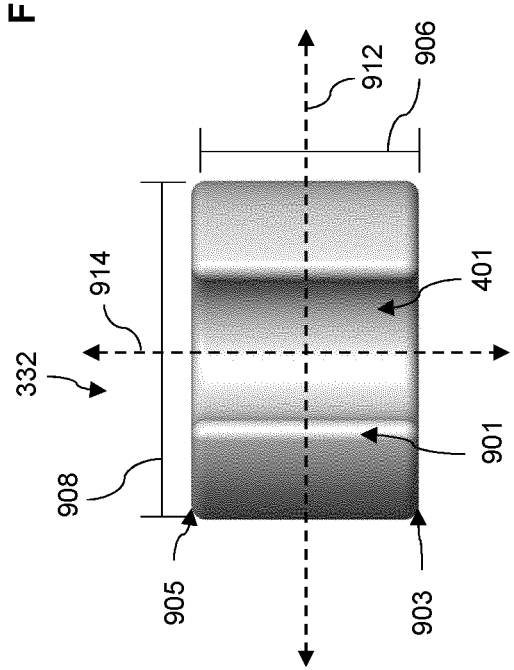

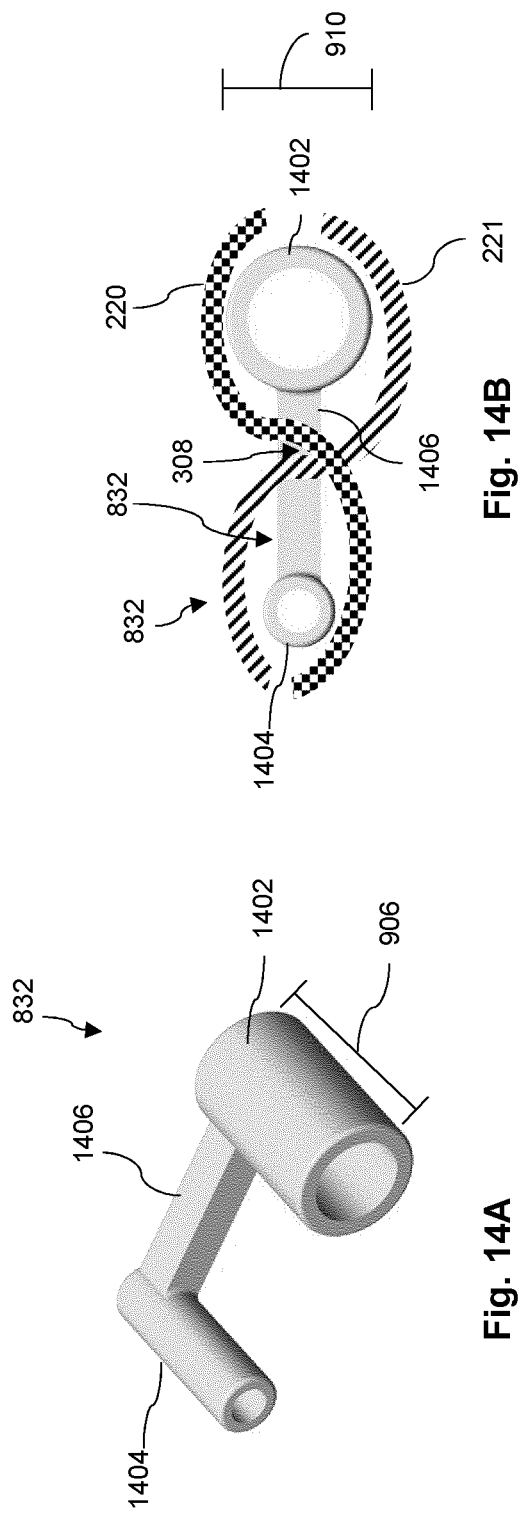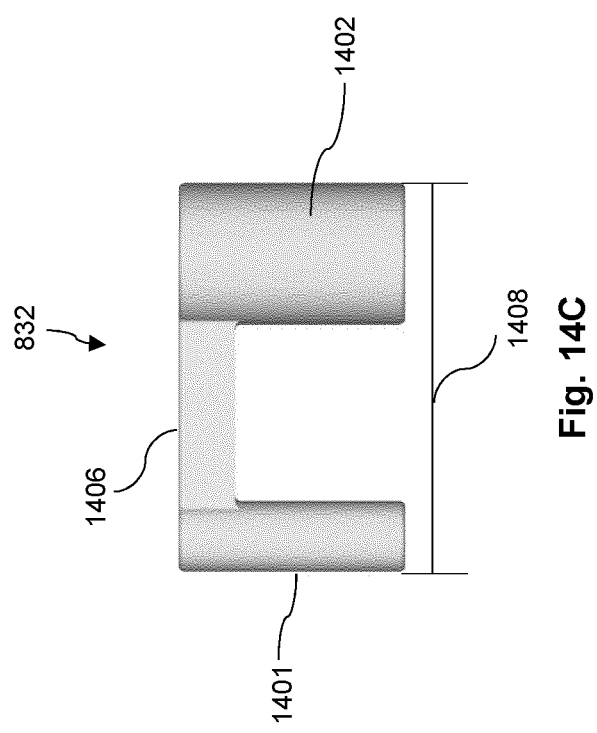
Fig. 14A
Fig. 14B
Fig. 14C

ULTRASOUND PROBE WITH CABLE RETENTION USING ELASTOMERIC INSERT

CROSS-REFERENCE TO PRIOR APPLICATIONS

This application is the U.S. National Phase application under 35 U.S.C. § 371 of International Application No. PCT/EP2020/064357, filed on May 25, 2020, which claims the benefit of U.S. Provisional Patent Application No. 62/852,460, filed on May 24, 2019. These applications are hereby incorporated by reference herein.

TECHNICAL FIELD

The present disclosure relates generally to the structural arrangement of an ultrasound probe, and in particular, to an elastomeric insert positioned within the ultrasound probe to prevent tensile damage on one or more electrical conductor bundles.

BACKGROUND

External ultrasound imaging devices have become indispensable diagnostic tools in modern day medical care due to their non-invasive nature and ever-increasing resolution. In a conventional ultrasound imaging probe, epoxy plugs (also called adhesive anchors) are employed inside the housing as a cable management technique to prevent tensile damage on electrical wires upon application of a force. Force could be mechanically imposed as a result of, e.g., user mishandling the ultrasound probe and/or a person accidentally tripping over the cable of the ultrasound probe. The adhesive anchors need to be precisely located to be an effective tensile anchor while not obstructing functionality of the device. However, such adhesive anchors have been shown to cause mispositioning and stiffness on the electrical conductors by creating hinge points. Instead of preventing electrical conductors from moving within the housing, the adhesive anchors have been shown to enhance the friction between the electrical wires and the walls of the housing. The insulation around the wires has been shown to wear away at this hinge point as a result of the friction between the electrical wires and the walls of the housing. The exposed bare wires can lead to electrical shorting and failure of the ultrasound probe. In addition, as a result of movement being constrained by the epoxy plug, the wires can work-harden at this hinge point and ultimately break at this location during normal use.

SUMMARY

The present application provides an improved ultrasound imaging probe that includes an elastomeric insert positioned between two bundles of electrical wires. The electrical wires are part of a cable that allows for communication between the ultrasound probe and a computer that generates the ultrasound images. The bundles of electrical wire are positioned relative to the elastomeric insert so that they extend an extra length within the ultrasound probe. When the cable experiences a force from, e.g., someone tripping over it, the extra length of the two bundles of electrical wire is pulled back, which compresses the elastomeric insert. After the force has been removed, the elastomeric insert un-compresses by itself and moves the two bundles of electrical wire back to their original position including the extra length. In this manner, only the extra length of the electrical wires gets pulled back by the sudden force. This advantageously protects the ends of the electrical wires that are connected to electronics within the ultrasound probe, while avoiding the problems caused by the epoxy plugs in conventional devices.

According to an exemplary embodiment, an ultrasound probe is provided. The ultrasound probe includes a housing configured for handheld operation by a user; a transducer array coupled to the housing and configured to obtain ultrasound data; a cable coupled to the housing, wherein the cable comprises a conduit and a plurality of electrical conductors in communication with the transducer array, wherein the plurality of electrical conductors comprises a distal portion disposed within the housing and a proximal portion disposed within the conduit; and an elastomeric insert disposed within the housing and comprising a compressed state and an uncompressed state, wherein the elastomeric insert is in contact with the plurality of electrical conductors such that application of a force on the cable causes the plurality of electrical conductors to compress the elastomeric insert into the compressed state and such that, upon cessation of the force on the cable, the elastomeric insert moves the plurality of electrical conductors while returning to the uncompressed state.

In some embodiments, the distal portion of the plurality of electrical conductors is arranged into a first bundle and a second bundle, and the first bundle is disposed on a first side of the elastomeric insert and the second bundle is disposed on an opposite, second side of the elastomeric insert. In some embodiments, the first bundle and second bundle comprise a x-shaped configuration. In some embodiments, a crossing of the first bundle and the second bundle in the x-shaped configuration is distal of the elastomeric insert, and the plurality of electrical conductors splits into the first bundle and the second bundle proximal of the elastomeric insert. In some embodiments, electronic circuitry disposed within the housing and in communication with the transducer array, wherein the first bundle and the second bundle are coupled to opposite sides of the electronic circuitry. In some embodiments, the ultrasound probe further comprises a first circuit board and a second circuit board disposed within the housing and in communication with the transducer array, wherein the first circuit board is positioned superiorly relative the second circuit board, wherein, at a proximal portion of the housing, the first bundle is positioned superiorly relatively to the second bundle, wherein the first bundle is coupled to the second circuit board and the second bundle is coupled to the first circuit board such that, along a length of the housing, the first bundle and the second bundle cross one another.

In some embodiments, the elastomeric insert comprises a first groove on the first side and a second groove on the second side, and the first bundle is disposed within the first groove and the second bundle disposed within the second groove. In some embodiments, the elastomeric insert comprises a slot disposed between the first groove and the second groove. In some embodiments, the elastomeric insert comprises a first body portion, a second body portion, and a connector extending therebetween. In some embodiments, the first bundle and second bundle are disposed on opposite sides of the connector. In some embodiments, the first bundle and the second bundle are disposed on opposite sides of the first body portion and opposite sides of the second body portion. In some embodiments, the distal portion of the plurality of electrical conductors is arranged into a first bundle and a second bundle, wherein the force on the cable acts in a longitudinal direction, the elastomeric insert, the first bundle, and the second bundle are structurally arranged such that the force on the cable in the longitudinal direction causes lateral movement of the first bundle and the second bundle to compress the elastomeric insert. In some embodiments, the elastomeric insert is disposed within a distal portion of the cable. In some embodiments, a shape of the elastomeric insert matches a shape of the distal portion of the cable. In some embodiments, the plurality of electrical conductors extends a first length within the housing when the elastomeric insert is in the uncompressed state, and the plurality of electrical conductors extends a shorter, second length within the housing when the elastomeric insert is in the compressed state.

According to an exemplary embodiment, a system is provided. The system includes an ultrasound probe, comprising: a housing configured for handheld operation by a user; a transducer array coupled to the housing and configured to obtain ultrasound data; a cable coupled to the housing, wherein the cable comprises a conduit and a plurality of electrical conductors in communication with the transducer array, wherein the plurality of electrical conductors comprises a distal portion disposed within the housing and a proximal portion disposed within the conduit; and an elastomeric insert disposed within the housing and comprising a compressed state and an uncompressed state, wherein the elastomeric insert is in contact with the plurality of electrical conductors such that application of a force on the cable causes the plurality of electrical conductors to compress the elastomeric insert into the compressed state and such that, upon cessation of the force on the cable, the elastomeric insert moves the plurality of electrical conductors while returning to the uncompressed state; and a computer in communication with the transducer array via the plurality of electrical conductors and configured to generate an ultrasound image based on the ultrasound data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8 is a diagrammatic perspective view of a portion of an elastomeric insert in uncompressed state, according to aspects of the present disclosure.

FIG. 9A is a diagrammatic perspective view of an elastomeric insert, according to aspects of the present disclosure.

FIG. 9B is a diagrammatic end view of the elastomeric insert of FIG. 9A.

FIG. 9C is a diagrammatic top view of the elastomeric insert of FIG. 9A.

FIG. 14A is a diagrammatic perspective view of an elastomeric insert, according to aspects of the present disclosure.

FIG. 14B is a diagrammatic side view of the elastomeric insert of FIG. 14A.

FIG. 14C is a diagrammatic top view of the elastomeric insert of FIG. 14A.

DETAILED DESCRIPTION

Figure 1:
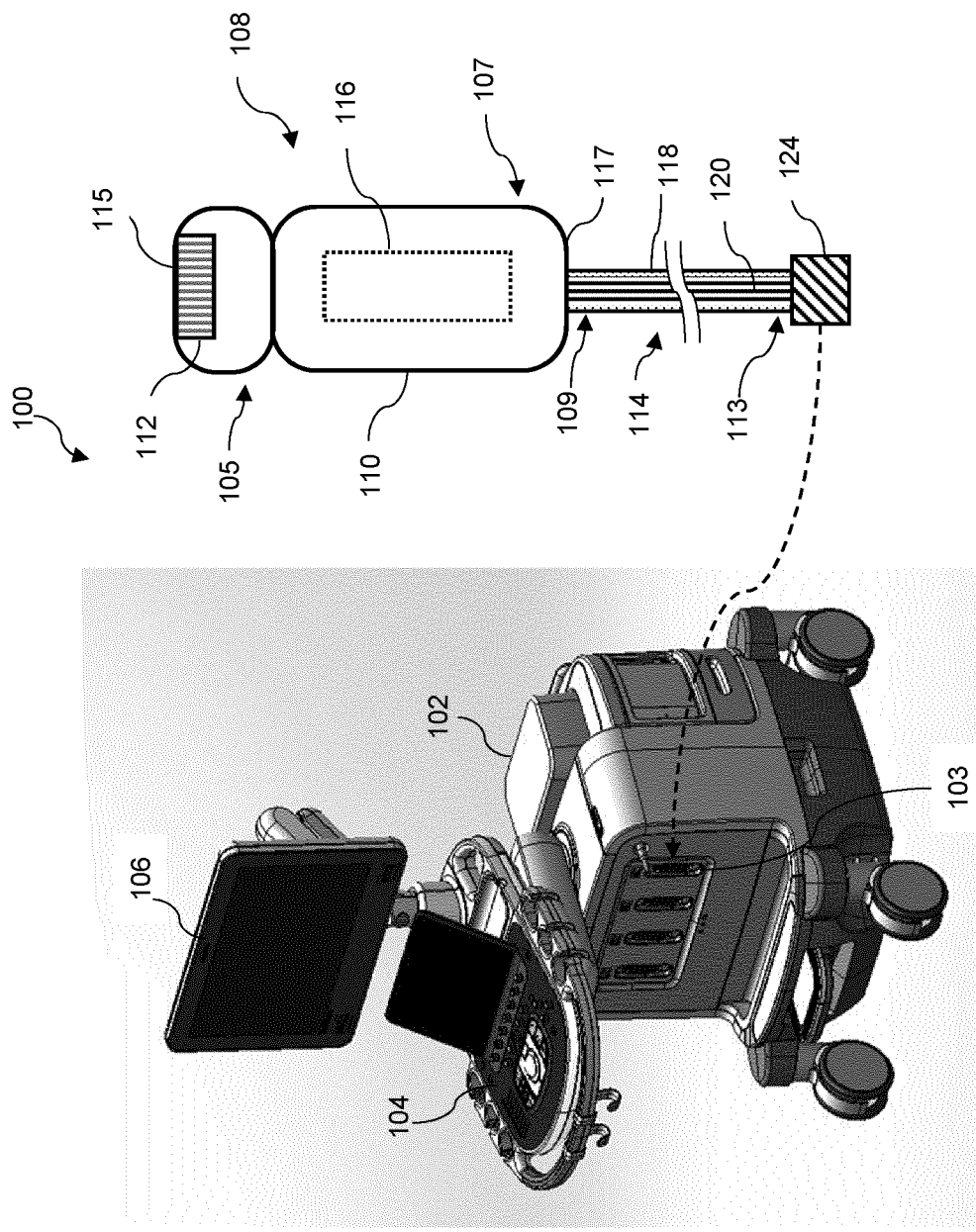
FIG. 1 is a diagrammatic perspective view of an ultrasound imaging system including a console and an ultrasound probe, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic perspective view of an ultrasound imaging system 100, according to aspects of the present disclosure. The ultrasound imaging system 100 includes a console 102 and an ultrasound probe 108. The ultrasound imaging system 100 may be used to obtain and display ultrasound images of anatomy. In some circumstances, the system 100 may include additional elements and/or may be implemented without one or more of the elements illustrated in FIG. 1.

The ultrasound probe 108 is sized and shaped, structurally arranged, and/or otherwise configured to be placed on or near the anatomy of a subject to visualize anatomy inside of the subject's body. The subject may be a human patient or animal. The ultrasound probe 108 may be positioned outside the body of the subject. In some embodiments, the ultrasound probe 108 is positioned proximate to and/or in contact with the body of the subject. For example, the ultrasound probe 108 may be placed directly on the body of the subject and/or adjacent to the body of the subject. The view of the anatomy shown in the ultrasound image depends on the position and orientation of the ultrasound probe 108. To obtain ultrasound data of the anatomy, the ultrasound probe 108 can be suitably positioned and oriented by a user, such as a physician, sonographer, and/or other medical personnel, so that a transducer array 112 emits ultrasound waves and receives ultrasound echoes from the desired portion of the anatomy. The ultrasound probe 108 may be portable and suitable for use in a medical setting. In some instances, the ultrasound probe 108 can be referenced as an ultrasound imaging device, a diagnostic imaging device, external imaging device, transthoracic echocardiography (TTE) probe, and/or combinations thereof.

The ultrasound probe 108 includes a housing 110 structurally arranged, sized and shaped, and/or otherwise configured for handheld grasping by a user. The housing 110 can be referenced as a handle in some instances. A proximal portion 107 of the housing 110 can be referenced as a handle in some instances. The housing 110 surrounds and protects the various components of the imaging device 108, such as electronic circuitry 116 and the transducer array 112. Internal structures, such as a space frame for securing the various components, may be positioned within the housing 110. In some embodiments, the housing 110 includes two or more portions which are joined together during manufacturing. The housing 110 can be formed from any suitable material, including a plastic, a polymer, a composite or combinations thereof.

The housing 110 and/or the ultrasound probe 108 includes the proximal portion 107 terminating at a proximal end 117 and a distal portion 105 terminating at a distal end 115. In some instances, the ultrasound probe 108 can be described as having the proximal portion 107 and the distal portion 105. An imaging assembly of the ultrasound probe 108, including the transducer array 112, is disposed at the distal portion 105. All or a portion of the imaging assembly of the ultrasound probe 108 can define the distal end 115. The transducer array 112 can be directly or indirectly coupled to the housing 110. The operator of the ultrasound probe 108 may contact the distal end 115 of the ultrasound probe 108 to the body of the patient such that the anatomy is compressed in a resilient manner. For example, the imaging assembly, including the transducer array 112, may be placed directly on or adjacent to the body of the subject. In some instances, the distal portion 105 is placed directly in contact with the body of the subject such that the transducer array 112 is adjacent to the body of the subject.

The ultrasound probe 108 is configured to obtain ultrasound imaging data associated with any suitable anatomy of the patient. For example, the ultrasound probe 108 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, such as an artery or a vein of a patient's vascular system, including cardiac vasculature, peripheral vasculature, neural vasculature, renal vasculature, and/or any other suitable lumen inside the body. In addition to natural structures, the ultrasound probe 108 may be used to examine man-made structures such as, but without limitation, heart valves, stents, shunts, filters and other devices.

The transducer array 112 is configured to emit ultrasound signals, and receive ultrasound echo signals corresponding to the emitted ultrasound signals. The echo signals are reflections of the ultrasound signals from anatomy with the subject's body. The ultrasound echo signals may be processed by the electronic circuitry 116 in the ultrasound probe 108 and/or in the console 102 to generate ultrasound images. The transducer array 112 is part of the imaging assembly of the ultrasound probe 108, including an acoustic window/lens and a matching material on a transmitting side of the transducer array 112, and an acoustic backing material on a backside of the transducer array 112. The acoustic window and the matching material have acoustic properties that facilitate propagation of ultrasound energy in desired directions (e.g., outwards, into the body of the patient) from the transmitting side of the transducer array 112. The backing material has acoustic properties that impede or limit propagation of ultrasound energy in undesired directions (e.g., inwards, away from the body of the patient) from the backside of the transducer array 112.

The transducer array 112 may include any number of transducer elements. For example, the array can include between 1 acoustic element and 10000 acoustic elements, including values such as 2 acoustic elements, 4 acoustic elements, 15 acoustic elements, 64 acoustic elements, 128 acoustic elements, 500 acoustic elements, 812 acoustic elements, 3000 acoustic elements, 9000 acoustic elements, and/or other values both larger and smaller. The transducer elements of the transducer array 112 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., arranged in one or more rows, one or more columns, and/or one or more orientations) can be uniformly or independently controlled and activated. The transducer array 112 can be configured to obtain one-dimensional, two-dimensional, and/or three-dimensional images of patient anatomy. The ultrasound transducer elements may be piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The transducer array 112 is in communication with (e.g., electrically coupled to) the electronic circuitry 116. The electronic circuitry 116 can be any suitable passive or active electronic components, including integrated circuits (ICs), for controlling the transducer array 112 to obtain ultrasound imaging data and/or processing the obtained ultrasound imaging data. For example, the electronic circuitry 116 can include one or more transducer control logic dies. The electronic circuitry 116 can include one or more application specific integrated circuits (ASICs). In some embodiments, one or more of the ICs can comprise a microbeamformer (µBF), an acquisition controller, a transceiver, a power circuit, a multiplexer circuit (MUX), etc. In some embodiments, the electronic circuitry 116 can include a processor, a memory, a gyroscope, and/or an accelerometer. The electronic circuitry 116 is disposed within the ultrasound probe 108 and surrounded by the housing 110.

The ultrasound probe 108 includes a cable 114 to provide signal communication between the console 102 and one or more components of the ultrasound probe 108 (e.g., the transducer array 112 and/or the electronic circuitry 116). The cable 114 includes multiple electrical conductors 120 configured to carry electrical signals between the console 102 and the ultrasound probe 108. The electrical conductors 120 can be bare wires surrounded by one or more layers of insulating materials. The insulating materials are typically polymer-based composites, nylon, and/or polyvinyl chloride (PVC) synthetic plastic polymer. For example, electrical signals representative of the imaging data obtained by the transducer array 112 can be transmitted from the ultrasound probe 108 to the console 102 via the electrical conductors 120. Control signals and/or power can be transmitted from the console 102 to the ultrasound probe 108 via the electrical conductors 120. The cable 114 and/or electrical conductors 120 may provide any type of wired connection, such as a proprietary connection, an Ethernet connection, a Universal Serial Bus (USB) connection of any version or a mini USB of any version.

The cable 114 can also include a conduit 118 surrounding the electrical conductors 120. The conduit 118 is shaped as a tube and used to protect and route the electrical conductors 120 in the cable 114 of the ultrasound imaging device 108. The conduit 118 can be flexible and made of polymer, plastic, metal, fiber, other suitable materials, and/or combinations thereof. The conduit 118 protects the electrical conductors 120 by preventing their direct exposure to outside elements. A distal portion 109 of the cable 114 is coupled to the proximal portion 107 of the housing 110 of the ultrasound probe 108.

A connector 124 is located at a proximal portion 113 of the cable 114. The connector 124 is configured for removably coupling with the console 102. Signal communication between the ultrasound probe 108 and the console 102 is established when the connector 124 is received within a receptacle 103 of the console 102. In that regard, the ultrasound probe 108 can be electrically and/or mechanically coupled to the console 102. The console 102 can be referenced as a computer or a computing device in some instances. The console 102 includes a user interface 104 and a display 106. The console 102 is configured to process the ultrasound imaging data obtained by the ultrasound probe 108 to generate an ultrasound image and output the ultrasound image on the display 106. A user can control various aspects of acquiring ultrasound imaging data by the ultrasound probe 108 and/or display of ultrasound images by providing inputs at the user interface 104. The imaging device 108 and the display 106 may be communicatively coupled directly or indirectly to the console 102.

One or more image processing steps can be completed by the console 102 and/or the ultrasound probe 108. The console 102 and/or the ultrasound probe 108 can include one or more processors in communication with memory. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory is a random access memory (RAM). In other embodiments, the memory is a cache memory (e.g., a cache memory of the processor), magnetoresistive RANI (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein.

While the console 102 is a movable cart in the illustrated embodiment of FIG. 1, it is understood that the console 102 can be a mobile device (e.g., a smart phone, a tablet, a laptop, or a personal digital assistant (PDA)) with integrated processor(s), memory, and display. For example, a touch-screen of the mobile device can be the user interface 104 and the display 106.

Figure 2:
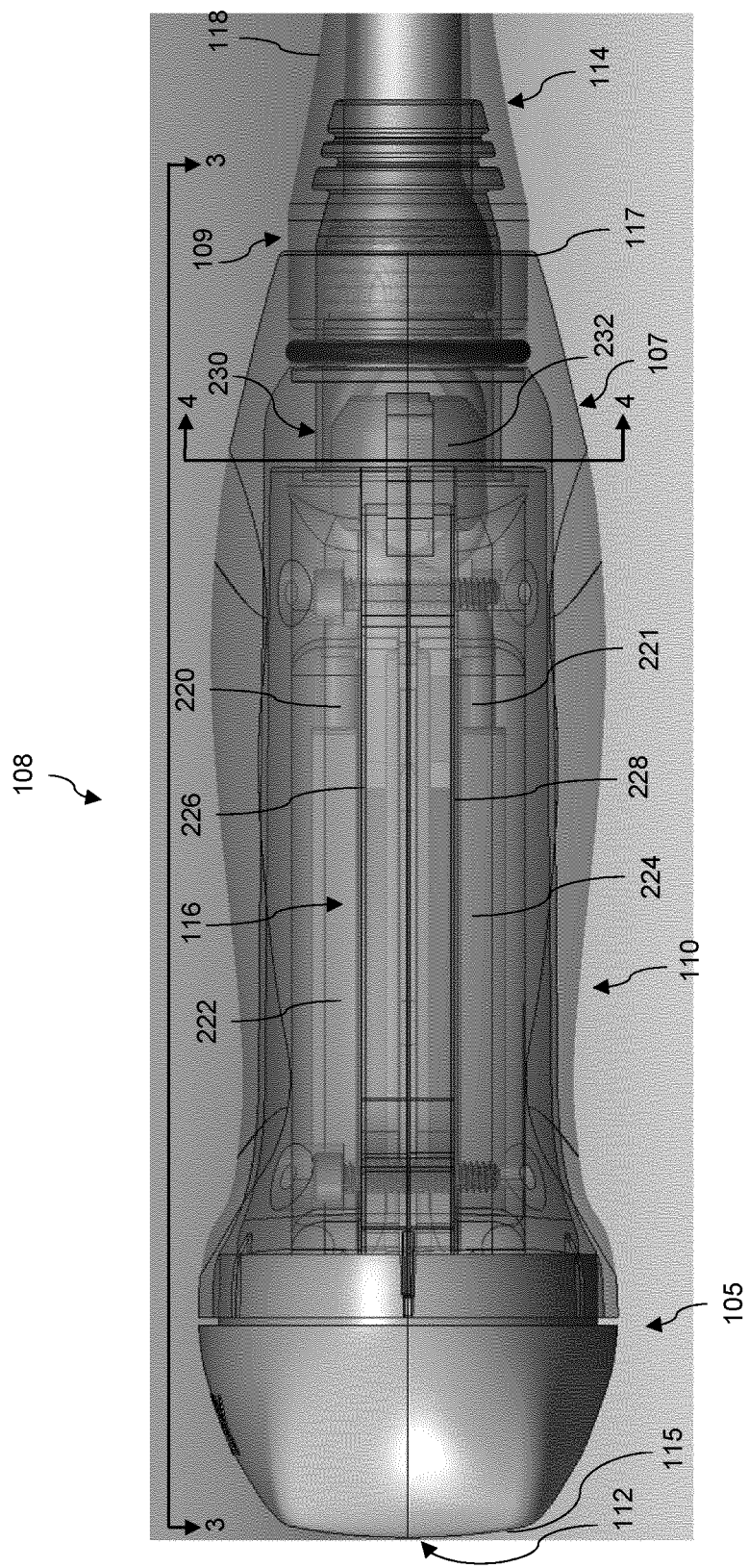
FIG. 2 is a diagrammatic, partially transparent side view of an ultrasound probe including an elastomeric insert, according to aspects of the present disclosure.
Figure 3:
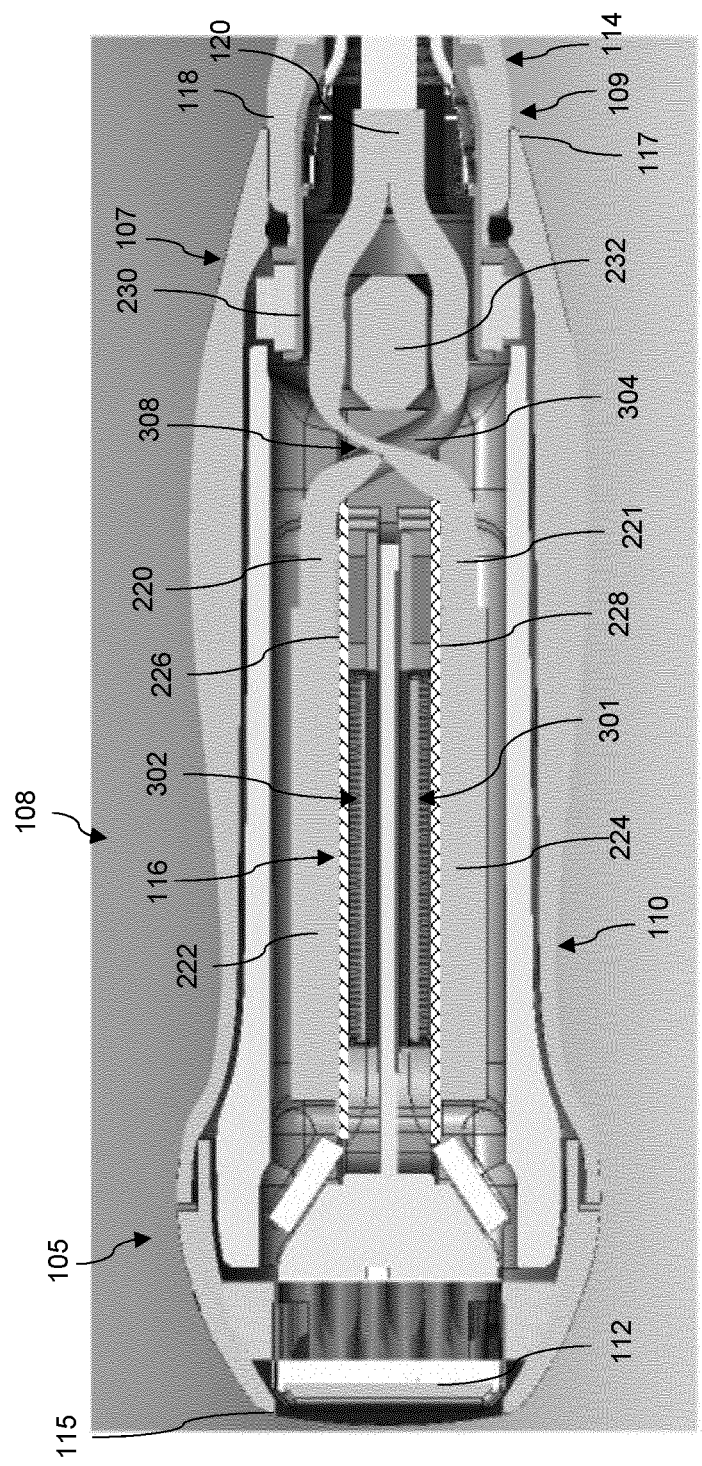
FIG. 3 is a diagrammatic, cross-sectional side view of the ultrasound probe along section line 3-3 in FIG. 2.
Figure 4:
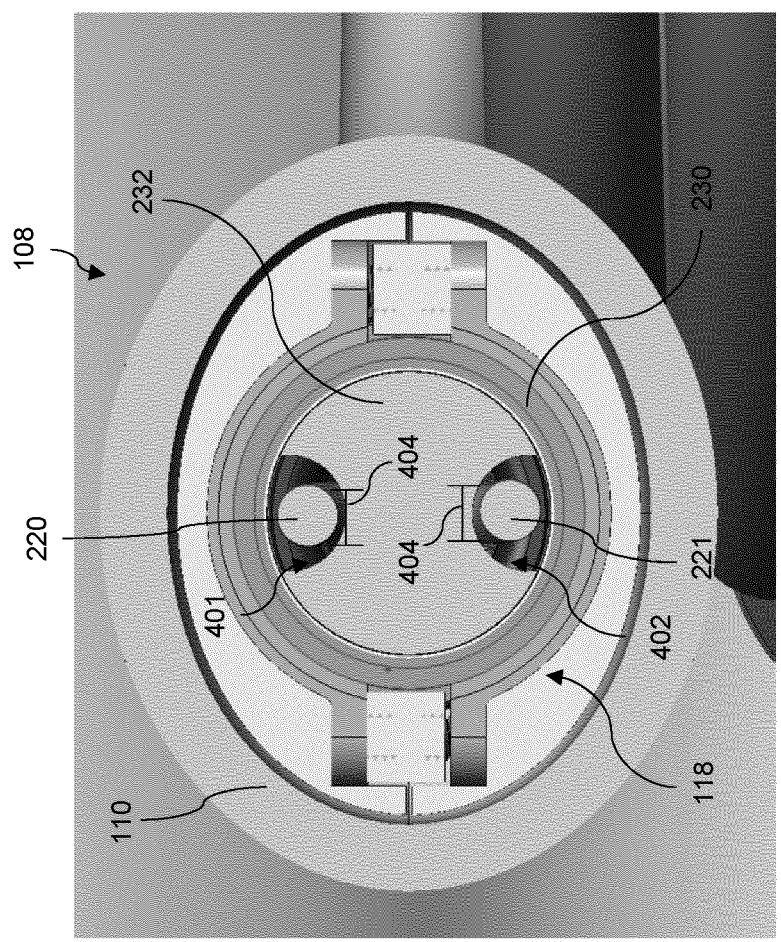
FIG. 4 is a diagrammatic, cross-sectional end view of the ultrasound probe along section line 4-4 in FIG. 2.
Figure 5:
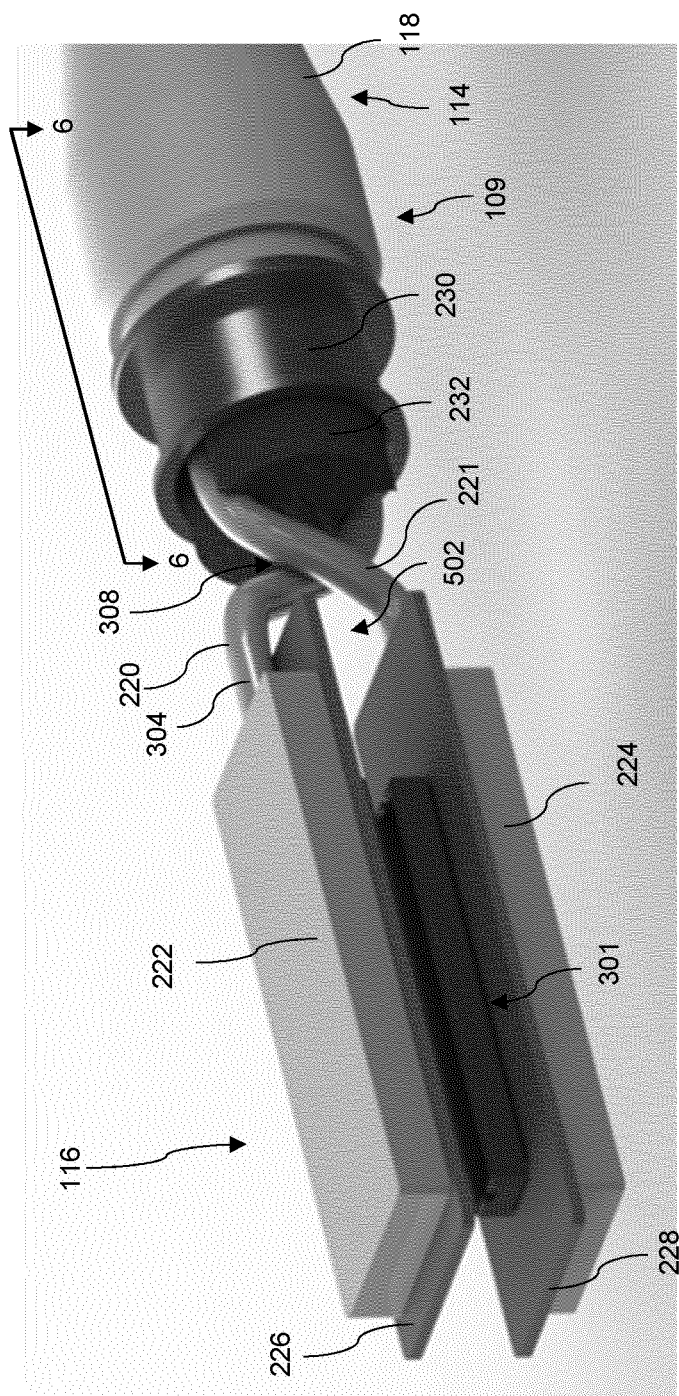
FIG. 5 is diagrammatic perspective view of a portion of an ultrasound probe including an elastomeric insert, according to aspects of the present disclosure.
Figure 6:
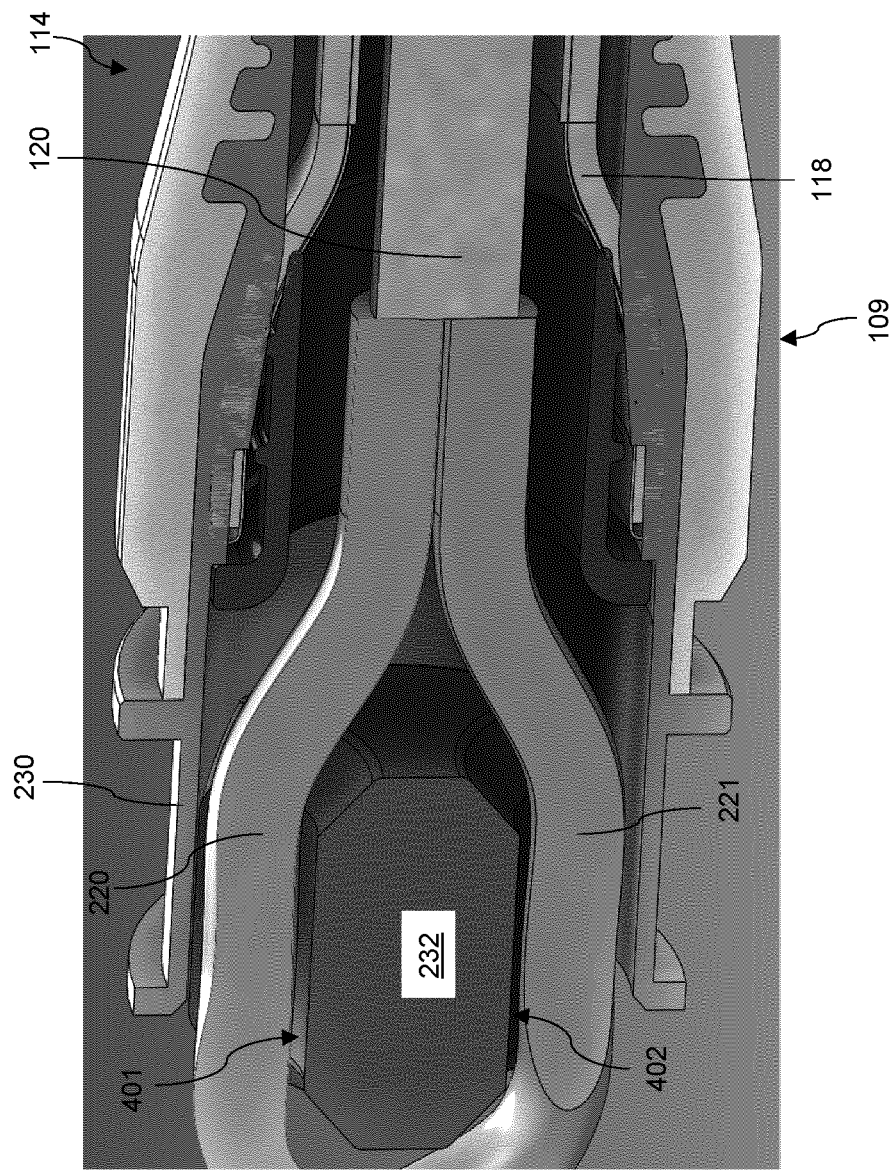
FIG. 6 is a diagrammatic, cross-sectional side view of the distal portion of a cable of the ultrasound probe along section line 6-6 in FIG. 5.

FIGS. 2-6 illustrate the structural arrangement of components of the ultrasound probe 108, according to aspects of the present disclosure. FIG. 2 is a diagrammatic, partially transparent side view of the ultrasound probe 108, including an elastomeric insert 232. FIG. 3 is a diagrammatic, cross-sectional side view of the ultrasound probe 108 along section line 3-3 in FIG. 2. FIG. 4 is a diagrammatic, cross-sectional end view of the ultrasound probe 108 along section line 4-4 in FIG. 2. FIG. 5 is diagrammatic perspective view of a portion of the ultrasound probe 108 including the elastomeric insert 232. FIG. 6 is a diagrammatic, cross-sectional side view of the distal portion 109 of the cable 114 of the ultrasound probe 108 along section line 6-6 in FIG. 5.

Various components of the ultrasound probe 108 are disposed within the housing 110. For example, the electronic circuitry 116, the distal portion 109 of the cable 114, and an elastomeric insert 232 are located inside the housing 110. The electronic circuitry 116 includes printed circuit boards (PCBs) 226, 228 (FIGS. 2, 3, 5), board to board electrical connectors 301, 302 (FIGS. 3, 5), and cable legs 220, 221 (FIGS. 2-6).

The cable 114 includes the conduit 118 surrounding the electrical conductors 120. The electrical conductors 120 are arranged as one unit along a majority of length of the cable 114 between the distal portion 109 of the cable 114 to proximal portion 113 of the cable 114. At the distal portion 109 of the cable 114, the single unit of electrical conductors 120 are split apart into two separate units forming cable legs 220, 221. In some instances, the cable legs 220, 221 can be referenced as bundles or subsets of the electrical conductors 120. In some embodiments, the division of the electrical conductors 120 into the cable legs 220, 221 occurs proximal of the elastomeric insert 232. For example, the split can be formed longitudinally at a ferrule 230, distal to the ferrule 230, or proximal to the ferrule 230. The ferrule 230 defines a distal end of the cable 114 and can be coupled to the conduit 118. In an exemplary embodiment, the ferrule 230 extends around the distal portion of the conduit 118 to provide increased strength and/or support and prevent splitting and/or wearing down of the conduit 118. The ferrule 230 can be shaped as cylindrical ring made from metal, polymer, or plastic. When the proximal portion 107 of the housing 110 surrounds the distal portion 109 of the cable 114, the ferrule 230 is located within the proximal portion 107 of the housing 110. In some embodiments, the division of the electrical conductors 120 into the cable legs 220, 221 can occur within the housing 110 and/or within the cable 114.

The split of the electrical conductors 120 is formed so that each cable leg 220 or 221 is connected to PCB 226 or 228. For example, the cable leg 220 is mechanically and electrically coupled to the PCB 226, and the cable leg 221 is mechanically and electrically coupled to the PCB 228. Each cable leg 220, 221 is formed as a subset of the plurality of electrical conductors 120. For example, the electrical conductors 120 are arranged into the cable legs 220, 221. Each cable leg 220, 221 includes a sleeve 304 surrounding the subset of electrical conductors 120. The sleeve 304 can be formed of any suitable material, such as a plastic or polymer, including polytetrafluoroethylene (PTFE) or Teflon. While two cable legs 220, 221 are shown in the illustrated embodiment, it is understood that the electrical conductors 120 can be arranged into any suitable number of cable legs, include one, three, four, or more. The cable legs 220, 221 can be a distal portion of the electrical conductors 120 that are at least partially positioned within the housing 110. More proximal portions of the electrical conductors 120 can be positioned within the conduit 118.

Electrical signals between the transducer array 112 and the cable 114 are communicated via the electronic circuitry 116. For example, the transducer array 112 and the cable legs 220, 221 are in communication with the PCBs 226 and 228. In particular, the distal ends of the electrical conductors 120 forming the cable legs 220 and 221, are mechanically and electrically coupled to the PCBs 226 and 228. For example, the distal ends of the electrical conductors 120 are soldered to the PCBs 226, 228. The material content of the solder is metal-based which permits electrical current to flow from one conductor to another within the electronic circuitry 116. The ultrasound probe 108 includes potting materials 222, 224 that can be formed from a polymer-based material to provide resistance to shock and vibration and prevent against moisture or corrosive agents on the electrical conductors 120. Potting material 222 is positioned over the terminations of the cable leg 220 at the PCB 226, and potting material 224 is positioned over the terminations of the cable leg 221 at the PCB 228. Various active and/or passive electronic components, such as the board to board connectors 301, 302, are mechanically and electrically coupled to the PCBs 226, 228. In the orientation shown in, e.g., FIGS. 3 and 5, the PCB 226 is positioned superiorly within the housing 110, and the PCB 228 is positioned inferiorly within the housing 110.

In conventional ultrasound imaging devices, the ferrule is typically filled with large plug of filler material. The filler material is formed of any suitable chemical adhesive or epoxy resin, such as polyepoxides, or reactive prepolymers and polymers which contain epoxide groups. In some instances, the filler material is referenced as an adhesive anchor, epoxy, or filler. The filler material is meant to prevent damages on the electrical conductors upon application of a force by preventing movement of the electrical conductors. Force could be mechanically imposed as a result of user mishandling the imaging device during usage. For example, such force can result when person trips over the cable of the imaging device. However, such filler materials have been shown to cause mis-positioning and stiffness of the electrical conductors and to create hinge point that coincides with damaged conductors. Further, instead of preventing electrical conductors from moving within the housing, the filler material has shown to enhance the friction between the electrical conductors and the walls of the housing. The friction causes bare wires to be exposed because the insulation coating wears out. The exposed bare wires can short.

Advantageously, this present disclosure provides an elastomeric insert 232 that eliminates the need for the epoxy plug. The elastomeric insert 232 is meant to serve as a shock absorber for the shock imposed on the electrical conductors 120 by the mechanical force as described earlier. The elastomeric insert 232 is disposed within the housing 110 at the proximal portion 107. As described herein, the elastomeric insert 232 can be used to direct, retain, and reposition the cable legs 220 and 221 and prevent damage on the electrical connections between the PCBs 226, 228 and the electrical conductors 120. When force is applied on the cable legs 220, 221 during usage the elastomeric insert 232 is compressed in a resilient manner and expands. The elastomeric insert 232 also absorbs any shock imposed on the electrical conductors 120 during usage. Once the force is removed, the elastomeric insert 232 returns to its original state and repositions the cable legs 220, 221 back into their original position. The original position of the cable legs 220, 221 may also be referred as neutral state herein. The elastomeric insert 232 can be formed of any suitable material with elastic properties such as a natural or synthetic polymer. Exemplary materials include solid silicone or urethane rubber, closed-cell foam silicone or urethane rubber, liquid silicone rubber (LSR), ethylene propylene diene monomer (EPDM), Santoprene™ thermoplastic vulcanizate (TPV), thermoplastic urethane (TPU), other suitable material, and/or combinations thereof. The elastomeric insert 232 can generally include a body with a cylindrical shape. In various embodiments, portions of the cylindrical body can be removed (e.g., grooves 401, 402 for the cable legs 220, 221). In some instances, the shape of the body of the elastomeric insert 232 can be described as a double-headed axe shape.

The proximal portion 107 of the housing 110 includes the elastomeric insert 232 and the ferrule 230. The elastomeric insert 232 and the cable legs 220 and 221 can be positioned within the ferrule 230. Generally, the elastomeric insert 232 can be positioned within the distal portion 109 of the cable 114. A shape of the elastomeric insert 232 can match a shape of the distal portion 109 of the cable 114. For example, when the ferrule 230 has a cylindrical lumen, the elastomeric insert 232 can be generally cylindrical such that the elastomeric insert 232 is disposed within the ferrule 230. For example, an outer surface of the elastomeric insert 232 can be shaped to contact and match the shape of the inner surface of the ferrule 230 and/or the distal portion of the cable 114. The elastomeric insert 232 can be positioned within the ferrule 230 with any suitable fit, such as an interference fit, press-fit, etc.

FIG. 5 illustrates an exemplary arrangement of the elastomeric insert 232. The elastomeric insert 232 can be positioned partially inside and partially outside of the ferrule 230. In some embodiments, a proximal portion (e.g., one-half or any suitable portion) of the elastomeric insert 232 can be positioned inside the ferrule 230 and a distal portion (e.g., one-half or any suitable portion) of the elastomeric insert 232 can be positioned outside of the ferrule 230. Both FIG. 3 and FIG. 5 illustrate embodiments in which the elastomeric insert 232 is positioned in between the cable legs 220 and 221. The cable legs 220 and 221 can be directed over and around the elastomeric insert 232 forming a crossed shape or an x-shape 308. For example, the crossing of the cable legs 220 and 221 to form the x-shape 308 can be distal of the elastomeric insert 232. For example, the cable legs 220 and 221 are coupled to opposite sides of the electronic circuitry 116. In the orientation shown in FIGS. 3 and 5, the cable leg 221 on the top (e.g., positioned superiorly) at the proximal portion 107 of the housing 110 becomes the cable leg 221 on the bottom (e.g., positioned inferiorly) more distally in the housing 110. Similarly, the cable leg 220 on the bottom (e.g., positioned inferiorly) at the proximal portion 107 of the housing 110 becomes the cable leg 220 on the top (e.g., positioned superiorly) more distally in the housing 110. Longitudinally, the elastomeric insert 232 is disposed between the x-shape 308 and the split of the electrical conductors 120 into the cable legs 220, 221.

The arrangement of the cable legs 220 and 221 with x-shape 308 and wrapping around or surrounding the elastomeric insert 232 effectively provides a service loop inside of the housing 110 where only minimal space is available. The arrangement also provides extra slack for the cable legs 220 and 221 to freely move inside the conduit 118. The extra slack will prevent tension and damage to the solder joints when external mechanical force is applied during usage. In that regard, when the elastomeric insert is in its uncompressed state, the cable legs 220 and 221 extend a greater length within the housing 110 than when the elastomeric insert 232 is in its compressed state. That is, force on the cable 114 shortens the length of the cable legs 220 and 221 within the housing 110 because the cable legs 220, 221 are pulled proximally. The elastomeric insert 232 absorbs the shock and automatically returns the cable legs 220 and 221 to their original configuration. In the original configuration, more length of the cable legs 220 and 221 is inside of the housing 110. This extra length provides the service loop for the electrical conductors 120 inside the housing 110, so that only this extra length is pulled by the force on the cable 114, rather than the solder joints between the electrical conductors 120 and the PCBs 226, 228. The presence of the elastomeric insert 232 prevents the effect of the applied force to be transferred to the electrical interconnections.

The cable leg 220 is disposed on a first side of the elastomeric insert 232 and the cable leg 221 is disposed on an opposite, second side of the elastomeric insert 232. The cross-sectional views in FIG. 4 and FIG. 6 illustrate cable legs 220 and 221 positioned inside the grooves 401 and 402 (FIG. 4) on opposite sides of the elastomeric insert 232. The dimensions of the grooves 401 and 402 include the circumference 404 of cable legs 220 and 221 in range between 0.10 to 0.25 inches in diameter. In some embodiments, the circumference 404 of the grooves 401 and 402 is slightly smaller than the circumference 404 of the cable legs 220 and 221 so that there is tight fitting between them. In some embodiment, the circumference 404 of the grooves 401 and 402 is equal or larger than the circumference 404 of the cable legs 220 and 221 (as shown in e.g., FIG. 4).

Figure 7:
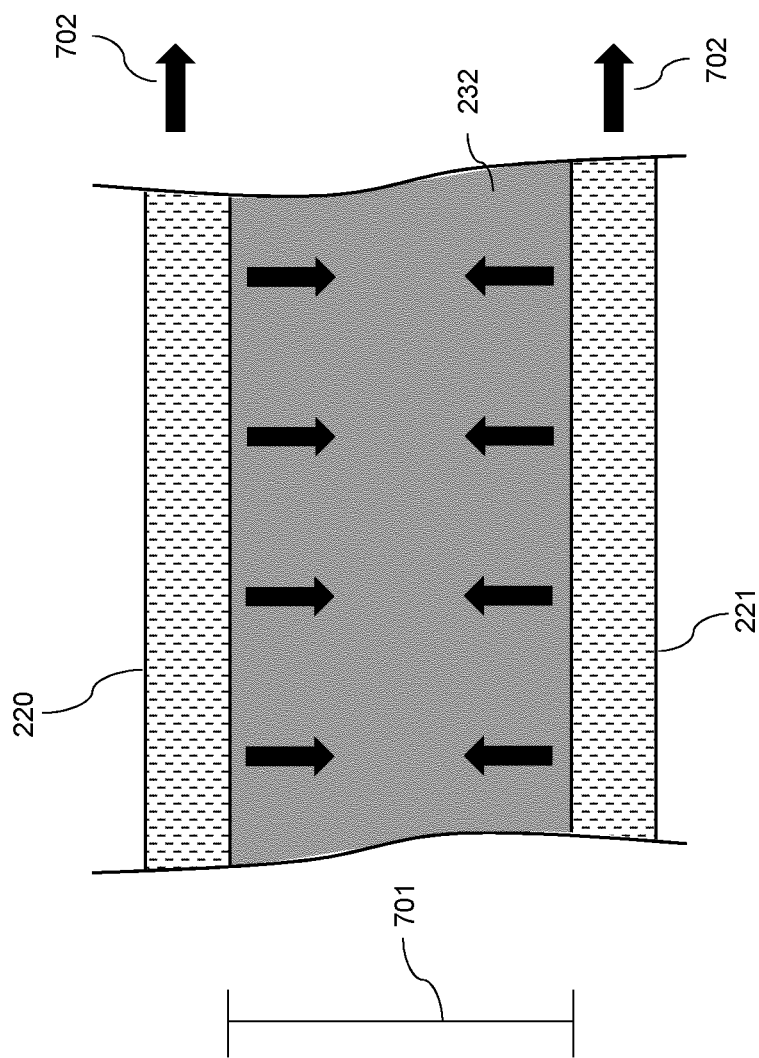
FIG. 7 is a diagrammatic perspective view of a portion of an elastomeric insert in compressed state, according to aspects of the present disclosure.

FIG. 7 and FIG. 8 illustrate the changes in state of the elastomeric insert 232 upon application and cessation of a force 702, according to aspects of the present disclosure. FIG. 7 is a diagrammatic perspective view of a portion of the elastomeric insert 232 in compressed state. During usage of the ultrasound probe 108, the cable 114 can be pulled so that the cable legs 220 and 221 experience the force 702, e.g., in the direction indicated by the arrow (FIG. 7). The force 702 can variously be described as a longitudinal force, a tensile force, and/or a force acting in the proximal direction. The longitudinal force 702 causes lateral movement of the cable legs 220, 221 (e.g., inward, towards one another). The cable legs 220 and 221 are in a x-shape 308 around the elastomeric insert 232. Because of that structural arrangement, the longitudinal force 702 causes the cable legs 220, 221 to move toward one another, which compresses the elastomeric insert 232. The elastomeric insert 232 has a height 701 in the compressed state.

FIG. 8 is a diagrammatic perspective view of a portion of the elastomeric insert 232 in uncompressed state. For example, upon cessation of force 702 acting upon cable legs 220 and 221, the material properties of the elastomeric insert 232 cause it to return to its original uncompressed height 801. The uncompressed height 801 is larger than the compressed height 701. In that regard, the elastomeric insert 232 is compressed in a resilient manner (FIG. 7) so that the elastomeric insert 232 returns to its original state. Expansion of the elastomeric insert 232 acts on the cable legs 220, 221 to move the cable legs 220, 221. For example, the expansion of the elastomeric insert 232 pushes the cable legs 220, 221 apart from one another.

To fabricate the exemplary elastomeric insert 232 disclosed herein, several different manufacturing techniques may be used based on material and structure of the elastomeric insert 232, including injection molding, casting, 3D printing, and/or other suitable techniques. It should be understood that no limitation to any particular manufacturing technology is intended or should be implied from the teachings of the disclosed principles.

FIGS. 9-14 illustrate embodiments of an elastomeric insert 232, according to aspects of the present disclosure. The particular structure and/or elastic properties of the elastomeric insert 232 can vary, but all embodiments are sized and shaped, structurally arranged, and/or otherwise configured to prevent tensile damage to the electrical interconnections within the ultrasound probe 108.

FIGS. 9A-9C illustrates an elastomeric insert 332, according to aspects of the present disclosure. FIG. 9A is a diagrammatic perspective view of the elastomeric insert 332. FIG. 9B is a diagrammatic end view of the elastomeric insert 332. FIG. 9C is a diagrammatic top view of the elastomeric insert 332. The elastomeric insert 332 is sized and shaped to be symmetrical about the x-axis 912 and the perpendicular y-axis 914. The elastomeric insert 332 includes fillet edges 901, side surface 904, and grooves 401 and 402. The side surface 904 can be in contact with an interior surface of the ferrule 230. FIG. 9C illustrates a groove surface of the groove 401. In various embodiments, the side surface 904 and/or the surface of the grooves 401, 402 can be smooth or textured. The dimensions of the grooves 401 and 402 can include the circumference 404 of the cable legs 220, 221. The grooves 401 and 402 can have semicircular shape. In some embodiments, the grooves 401 and 402 shape can be another curved or polygonal shape. The grooves 401, 402 extend longitudinally, from a proximal surface 903 to a distal surface 905 of the elastomeric insert 332.

The elastomeric insert 332 is formed with slot 902 including of full radii and round edges on both ends, as illustrated in FIG. 9B. The slot 902 is disposed between the grooves 401, 402. The middle slot 902 provides increased elastic properties and flexibility for the elastomeric insert 332. For example, adding the middle slot 902 allows the use of higher durometer materials, which can provide more durability and ease of processing of the raw material. The ability to utilize higher durometer materials with the middle slot 902 increases assurance of supply by not limiting the elastomeric insert 332 to a narrow range of material options. The middle slot 902 is formed extending longitudinally from the proximal surface 903 to the distal surface 905 of the elastomeric insert 332. A width 906 of the elastomeric insert 332 can be between approximately 0.5 inch and 3 inches, and/or other suitable values both larger and smaller, for example. A length 908 of the elastomeric insert 332 can be between approximately 0.25 inches and 1 inch, and/or other suitable values both larger and smaller, for example. A height 910 of the elastomeric insert 332 can be between approximately 0.25 inches and 1 inch, and/or other suitable values both larger and smaller, for example.

Figure 10:
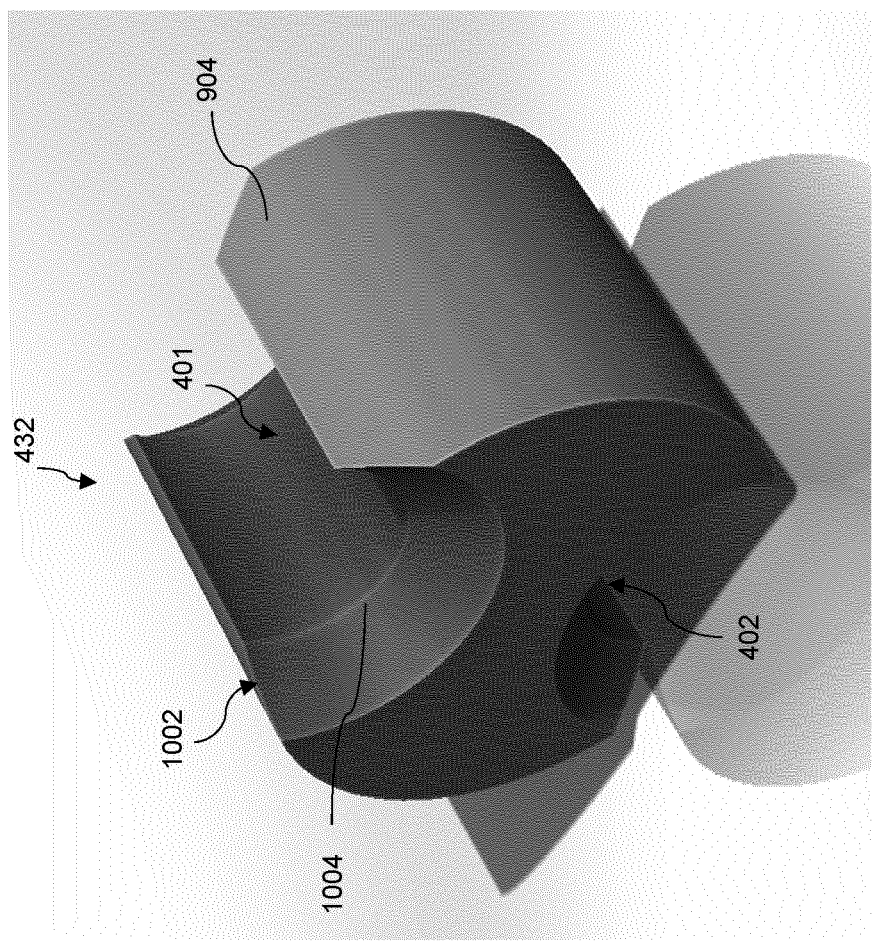
FIG. 10 is a diagrammatic perspective view of an elastomeric insert, according to aspects of the present disclosure.

FIG. 10 is a diagrammatic, perspective view of an elastomeric insert 432, according to aspects of the present disclosure. The elastomeric insert 432 includes chamfer edges 1002 and grooves 401, 402 with stepped surface 1004. In some embodiments, the stepped surface 1004 allows for the cable legs 220 and 221 to be more accurately and/or easily set into the grooves 401, 402. The step or chamfered edge 1002 breaks the sharp edge of the elastomeric insert 432, which allows for a smoother and unconstrained transition, and eliminates a potential pinch point for the cable legs 220, 221 as they pass over and across the elastomeric insert 432. Elastomeric insert 432 can include similar dimensions as elastomeric insert 332 of FIG. 9. The elastomeric insert 432 is solid in the middle and does not include a slot as in FIGS. 9A-9C. The elastomeric insert 432 with solid middle configuration can have different elastic properties then the elastomeric insert 332 from FIG. 9. In some instances, elastomeric inserts 332, 432 can have similar elastic properties. For example, the elastomeric insert 432 (without a slot) can be made of a lower durometer material and the elastomeric insert 332 (including the slot 902) can be made of a higher durometer material.

Figure 11:
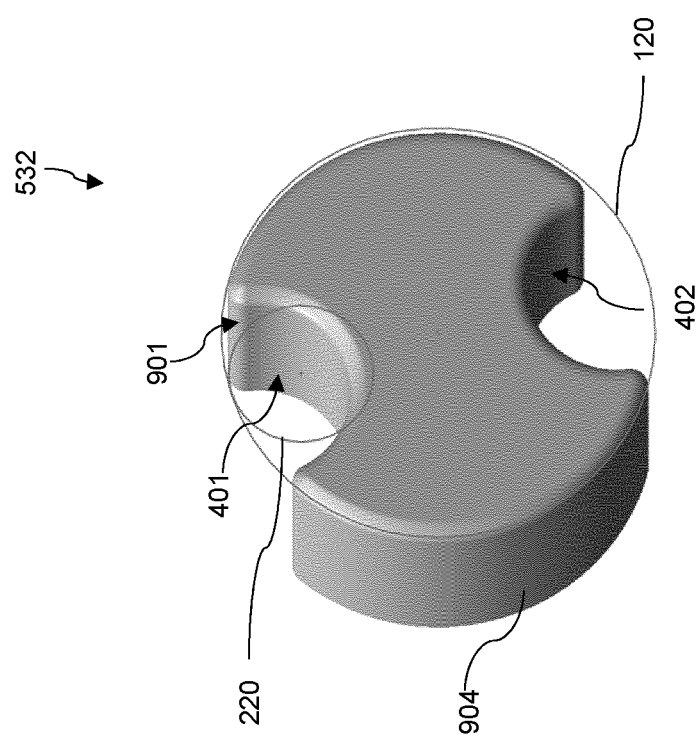
FIG. 11 is a diagrammatic perspective view of an elastomeric insert, according to aspects of the present disclosure.

FIG. 11 is a diagrammatic, perspective view of an elastomeric insert 532, according to aspects of the present disclosure. The elastomeric insert 532 can include some features similar to the elastomeric insert 332 of FIG. 9. The elastomeric insert 532 includes fillet edges 901, as well as grooves 401 and 402, and side surface 904. However, the illustrated embodiment differs from that of FIG. 9 in that the elastomeric insert 532 is formed without a slot, as illustrated. The exemplary positioning of the cable leg 220 within the groove 401 is illustrated. While only one outline for the cable leg 220 in groove 401 is shown, it is understood that the cable leg 221 is positioned within the groove 402.

Figure 12:
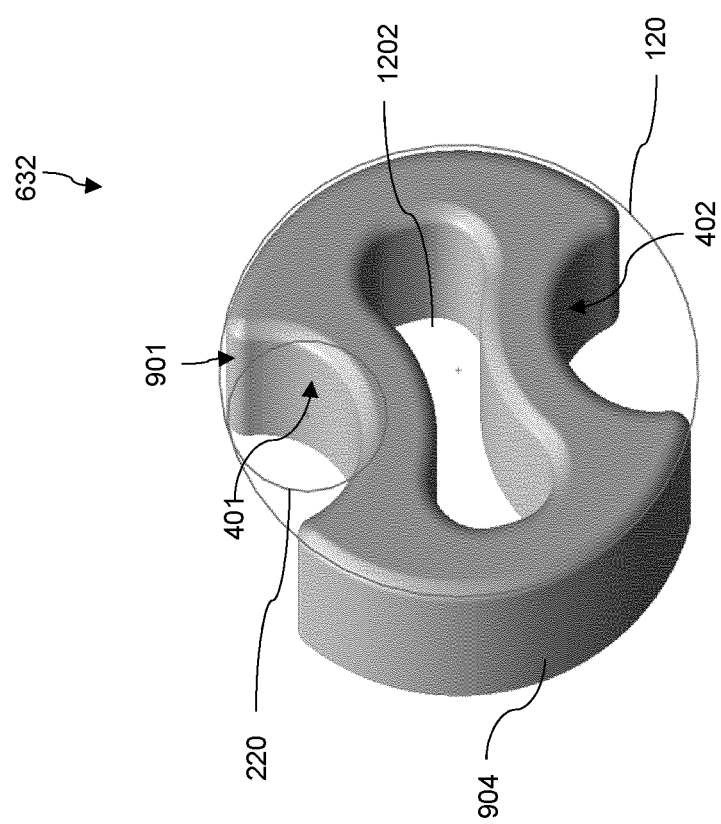
FIG. 12 is a diagrammatic perspective view of an elastomeric insert, according to aspects of the present disclosure.

FIG. 12 is a diagrammatic, perspective view of an elastomeric insert 632, according to aspects of the present disclosure. The elastomeric insert 632 can include some features similar to the elastomeric insert 332 of FIG. 9. Specifically, this exemplary embodiment 632 includes a fillet edges 901, as well as grooves 401 and 402, and side surface 904. However, this embodiment differs from that of FIG. 9 in that the elastomeric insert 632 is formed with a slot having a dog-bone shape 1202, as illustrated. The dog-bone shaped slot 1202 is formed with smaller height in the middle of the slot and larger height at the lateral ends of the slot. In some instances, the dog-bone shape 1202 can provided increased elasticity of the elastomeric insert 632 compared to the elastomeric insert 332 in FIG. 9. The dog-bone shape 1202 further increases assurance of supply by not limiting the elastomeric insert 632 to a narrow range of material options and design tradeoffs. Similar to the slot 902 (FIG. 9), adding the dog-bone shape slot 1202 allows the use of higher durometer materials, which can provide more durability and ease of processing of the raw material. The exemplary positioning of the cable leg 220 within the groove 401 is illustrated. While only one outline for the cable leg 220 in groove 401 is shown, it is understood that the cable leg 221 is positioned within the groove 402.

Figure 13:
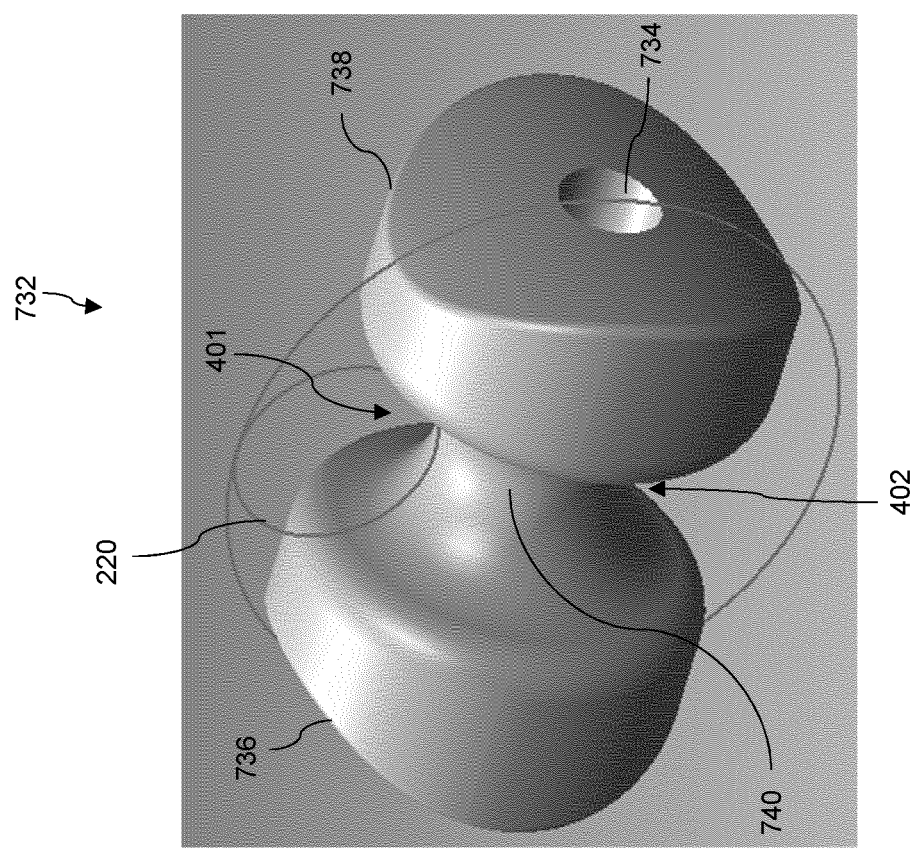
FIG. 13 is a diagrammatic perspective view of an elastomeric insert, according to aspects of the present disclosure.

FIG. 13 is a diagrammatic, perspective view of an elastomeric insert 732, according to aspects of the present disclosure. Elastomeric insert 732 can have similar dimensions as the elastomeric insert 332 of FIG. 9. This elastomeric insert 732 includes a dumbbell shape formed by two larger body portions 736, 738 and a central, linking portion 740 extending between them. In that regard, the body portions 736, 738 can be positioned laterally relatively to one another, with the linking portion 740 extending laterally between the two. The body portions 736, 738 can contact opposite portions of the inner surface of the distal portion 109 of the cable 114, e.g., the ferrule 230. The spaces between the larger body portions 736, 738 and the central linking portion 740 define the grooves 401, 402 in which the cable legs 220, 221 are positioned. For example, the cable legs 220, 221 can be disposed on opposite sides (e.g., top and bottom) of the central, linking portion 740. The exemplary positioning of the cable leg 220 within the groove 401 is illustrated. While only one outline for the cable leg 220 in groove 401 is shown, it is understood that the cable leg 221 is positioned within the groove 402. A slot 734 extends laterally, along the width of the elastomeric insert 732.

FIGS. 14A-14C illustrates an elastomeric insert 832, according to aspects of the present disclosure. FIG. 14A is a diagrammatic perspective view of the elastomeric insert 832 constructed. FIG. 14B is a diagrammatic side view of the elastomeric insert 832. FIG. 14C is a diagrammatic top view of the elastomeric insert 832. The elastomeric insert 832 includes body portions 1402 and 1404, and a linking portion 1406 formed to connect the two body portions 1402 and 1404. The body portions 1402 and 1404 can be hollow cylinders in some embodiments. The linking portion 1406 can be shaped as rectangular prism in some embodiments. In the illustrated embodiment, the cylinder 1402 is larger than the cylinder 1404.

The elastomeric insert 832 can be positioned within the housing 110, the ferrule 230, and/or the distal portion 109 of the cable 114 such that the cylinder 1402 is positioned longitudinally more proximally and the cylinder 1404 is positioned longitudinally more distally. In some embodiments, the hollow cylinder 1402 can be positioned at least partially inside the ferrule 230, similar to positioning of the elastomeric insert 232 (FIGS. 3 and 5). In some embodiments, the hollow cylinder 1404 can be positioned in the space 502 (FIG. 5), between the x-shape 308 and the proximal end of the PCBs 226, 228. In that regard, the crossing of the cable legs 220, 221 to form the x-shape 308 occurs between the cylinders 1402, 1404. As shown in FIG. 14B, the cable leg 220, 221 can be positioned on opposite sides of both the cylinder 1402 and 1404. For example, the cable leg 220 can be positioned over the cylinder 1402 and under the cylinder 1404. For example, the cable leg 221 is positioned under the cylinder 1402 and over the cylinder 1404.

A width 906 of the elastomeric insert 832 can be between approximately 0.25 inch and 0.5 inches, and/or other suitable values both larger and smaller, for example. A length 1408 of the elastomeric insert 832 can be between approximately 0.5 inches and 2 inches, and/or other suitable values both larger and smaller, for example. A height 910 of the elastomeric insert 832 can be between approximately 0.25 inches and 1 inch, and/or other suitable values both larger and smaller, for example.

The structure of the elastomeric insert 232 may be selected based on the size and/or type of imaging device 108 used for the ultrasound imaging system 100. Thus, any advantageous structural arrangement with appropriate length, width, and height, may be employed, which could include not only the circular/cylindrical and semi-circular shapes discussed herein, but also triangular, conic and rectilinear shapes may also be employed. The electrical conductors 120 may be directly wrapped around and surrounding the elastomeric insert 232 to form an x-shape 308. All exemplary variations of the elastomeric insert 232 in FIGS. 9-14 may be inserted into the housing 110, the ferrule 230, and/or the distal portion 109 of the cable 114. The elastomeric insert eliminates the need for epoxy plugs, which advantages removes a source of damage to the electrical conductors 120 and extend the life-cycle of ultrasound imaging device 108.

What is claimed is:

1. An ultrasound probe, comprising:
  a housing configured for handheld operation by a user;
  a transducer array coupled to the housing and configured to obtain ultrasound data;
  a cable coupled to the housing, wherein the cable comprises a conduit and a plurality of electrical conductors in communication with the transducer array, wherein the plurality of electrical conductors comprises a distal portion disposed within the housing and a proximal portion disposed within the conduit; and an elastomeric insert disposed within the housing and comprising a compressed state and an uncompressed state, wherein the elastomeric insert is in contact with the plurality of electrical conductors such that application of a force on the cable causes the plurality of electrical conductors to compress the elastomeric insert into the compressed state and such that, upon cessation of the force on the cable, the elastomeric insert moves the plurality of electrical conductors while returning to the uncompressed state, wherein the distal portion of the plurality of electrical conductors is arranged into a first bundle and a second bundle, and the first bundle is disposed on a first side of the elastomeric insert and the second bundle is disposed on an opposite, second side of the elastomeric insert.

2. The ultrasound probe of claim 1, wherein the first bundle and second bundle comprise a x-shaped configuration.

3. The ultrasound probe of claim 2, wherein:
a crossing of the first bundle and the second bundle in the x-shaped configuration is distal of the elastomeric insert, and
the plurality of electrical conductors is arranged into the first bundle and the second bundle proximal of the elastomeric insert.

4. The ultrasound probe of claim 2, further comprising:
electronic circuitry disposed within the housing and in communication with the transducer array, wherein the first bundle and the second bundle are coupled to opposite sides of the electronic circuitry.

5. The ultrasound probe of claim 1,
further comprising a first circuit board and a second circuit board disposed within the housing and in communication with the transducer array, wherein the first circuit board is positioned superiorly relative the second circuit board,
wherein, at a proximal portion of the housing, the first bundle is positioned superiorly relatively to the second bundle,
wherein the first bundle is coupled to the second circuit board and the second bundle is coupled to the first circuit board such that, along a length of the housing, the first bundle and the second bundle cross one another.

6. The ultrasound probe of claim 1, wherein:
the elastomeric insert comprises a first groove on the first side and a second groove on the second side, and
the first bundle is disposed within the first groove and the second bundle disposed within the second groove.

7. The ultrasound probe of claim 6, wherein the elastomeric insert comprises a slot disposed between the first groove and the second groove.

8. The ultrasound probe of claim 1, wherein the elastomeric insert comprises a first body portion, a second body portion, and a connector extending therebetween.

9. The ultrasound probe of claim 8, wherein the first bundle and second bundle are disposed on opposite sides of the connector.

10. The ultrasound probe of claim 8, wherein the first bundle and the second bundle are disposed on opposite sides of the first body portion and opposite sides of the second body portion.

11. The ultrasound probe of claim 1, wherein:
the distal portion of the plurality of electrical conductors is arranged into a first bundle and a second bundle,
wherein the force on the cable acts in a longitudinal direction,
the elastomeric insert, the first bundle, and the second bundle are structurally arranged such that the force on the cable in the longitudinal direction causes lateral movement of the first bundle and the second bundle to compress the elastomeric insert.

12. The ultrasound probe of claim 1, wherein the elastomeric insert is disposed within a distal portion of the cable.

13. The ultrasound probe of claim 1, wherein a shape of the elastomeric insert matches a shape of the distal portion of the cable.

14. The ultrasound probe of claim 1, wherein:
the plurality of electrical conductors extends a first length within the housing when the elastomeric insert is in the uncompressed state, and
the plurality of electrical conductors extends a shorter, second length within the housing when the elastomeric insert is in the compressed state.

15. A system, comprising:
an ultrasound probe, comprising:
a housing configured for handheld operation by a user;
a transducer array coupled to the housing and configured to obtain ultrasound data;
a cable coupled to the housing, wherein the cable comprises a conduit and a plurality of electrical conductors in communication with the transducer array, wherein the plurality of electrical conductors comprises a distal portion disposed within the housing and a proximal portion disposed within the conduit; and
an elastomeric insert disposed within the housing and comprising a compressed state and an uncompressed state, wherein the elastomeric insert is in contact with the plurality of electrical conductors such that application of a force on the cable causes the plurality of electrical conductors to compress the elastomeric insert into the compressed state and such that, upon cessation of the force on the cable, the elastomeric insert moves the plurality of electrical conductors while returning to the uncompressed state; and
a computer in communication with the transducer array via the plurality of electrical conductors and configured to generate an ultrasound image based on the ultrasound data,
wherein
the distal portion of the plurality of electrical conductors is arranged into a first bundle and a second bundle, and
the first bundle is disposed on a first side of the elastomeric insert and the second bundle is disposed on an opposite, second side of the elastomeric insert.

* * * * *